United States Patent [19]

Gross et al.

[11] Patent Number: 4,959,134

[45] Date of Patent: Sep. 25, 1990

[54] PROCESS AND APPARATUS FOR ELECTROPHORETIC DETERMINATION OF PRIMARY STRUCTURE OF NUCLEIC ACIDS

[75] Inventors: Valery N. Gross; Evgeny V. Kozhanov, both of Alma-Ata; Murat A. Aitkhozhin, deceased, late of Alma-Ata, by Galina T. Darkanbaeva, administrator; David R. Beritashvili, Moscow; Evgeny N. Tverdokhlebov, Moscow; Georgy P. Georgiev, Moscow, all of U.S.S.R.

[73] Assignee: Institut Molekulyarnoy Biologii I Biokhimii Akademii Nauk KazSSR, Alma-ata, U.S.S.R.

[21] Appl. No.: 272,622

[22] Filed: Nov. 17, 1988

[30] Foreign Application Priority Data

Nov. 27, 1987 [SU] U.S.S.R. .............. 4329887[U]

[51] Int. Cl.$^5$ ............................................ G01N 27/26
[52] U.S. Cl. .............................. 204/182.8; 204/299 R
[58] Field of Search .................... 204/299 R, 182.8

[56] References Cited

U.S. PATENT DOCUMENTS 4,624,769 11/1986 Simada et al. .................. 204/299 R
4,642,169 2/1987 Yoshisato et al. .............. 204/299 R
4,810,183 3/1989 Place et al. ..................... 204/299 R

*Primary Examiner*—John F. Niebling
*Assistant Examiner*—David G. Ryser
*Attorney, Agent, or Firm*—Burgess, Ryan & Wayne

[57] ABSTRACT

An apparatus and process is provided for an electrophoretic determination of the primary structure of nucleic acids. The apparatus comprises a cuvette shaped as a sleeve having a gel shaped as a hollow cylinder positioned on one of the side surfaces of the sleeve and having samples of the nucleic acid in recesses on its end face located in a circle. The sleeve is provided with a rotation drive and its side wall and the bottom together with the side wall and the bottom of the second sleeve mounted coaxially with the first sleeve form chambers for placing electrode solutions therein. Between the electrode solutions in the region between the side walls of the sleeves there is located a non-polar liquid, its density is higher than that of the electrode solution located above it and lower than the density of the electrode solution located thereunder. In the chambers annular electrodes are provided and a heat-exchanger in the non-polar liquid which maintains, through the non-polar liquid, the temperature of the gel shaped as a hollow cylinder at a predetermined level.

16 Claims, 4 Drawing Sheets

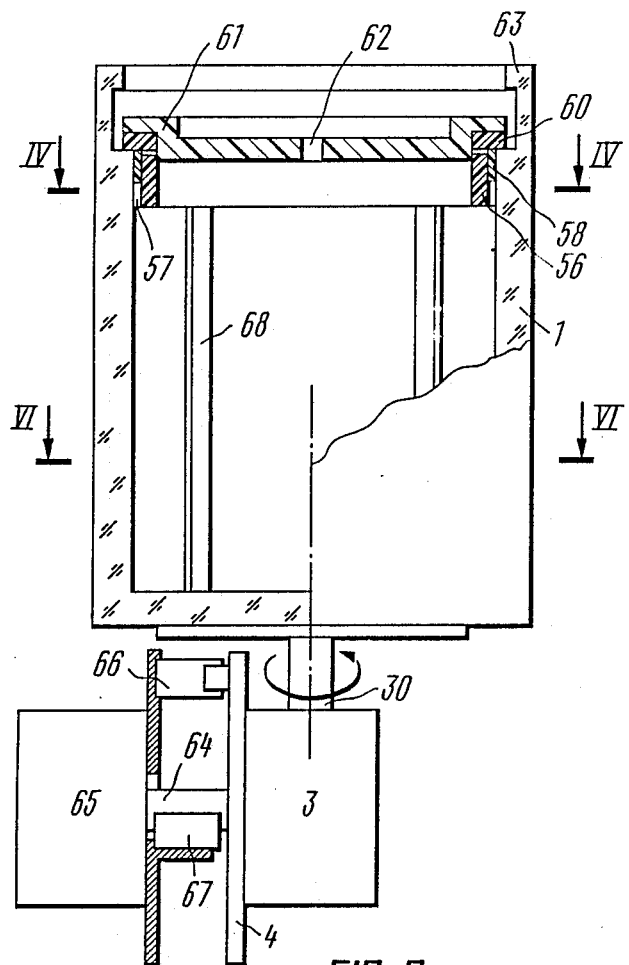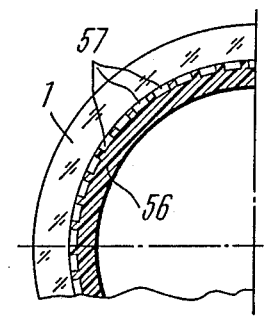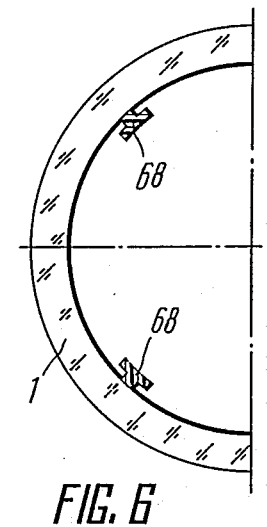
FIG. 3
FIG. 4
FIG. 6

PROCESS AND APPARATUS FOR ELECTROPHORETIC DETERMINATION OF PRIMARY STRUCTURE OF NUCLEIC ACIDS

FIELD OF THE INVENTION

The present invention relates to electrophoretic methods and, more specifically, to a process and apparatus for electrophoretic determination of the primary structure of nucleic acids.

The present invention can be useful in molecular biology and biotechnology.

PRIOR ART

The progress of methods for the determination of the primary structure-sequencing of DNA and RNA determines to a great extent the success of the genetic engineering employed in molecular biology studies and in biotechnology. In turn, the progress in medical care of the population and efficiency of agriculture depends to a great extent on the progress of research in determining the primary structure of DNA and RNA.

The sequencing of DNA and RNA makes it possible to find out the structure of individual genes of an animal, vegetable or bacterial genome. Since functional properties of biological molecules are defined by their structure, the knowledge of the latter makes it possible to construct mole cules with predetermined properties. Microorganisms into which the required genes can be introduced might become "factories" for the production of large quantities of pharmaceuticals, growth hormones and other useful products.

The need for considerable improvement of the existing procedure of sequencing has emerged due to the necessity of decoding of human beings, domestic animals, plants and certain microorganisms. The results of this work can have two very important consequences. On the one hand, the knowledge of the structure of the entire genome can provide valuable material for the research into the organization of the heriditary information in the live organism and regularities of its realization. It will be also possible to regularize numerous experimental data obtained, for example, in the molecular biology over the preceding years. In addition to its merely scientific signficance, the sequencing of genomes will open now practical opportunities. It will become possible to reconstruct both individual genes and groups of genes for the purpose, for example, of curing hereditary human diseases, improving resistance of useful plants or enhancing productivity of domestic animals and farm crops. It is also important that, in constrast to conventional medical and selection techniques, the genetic engineering approach makes it possible to attain practically useful results within substantially shorter time limits.

The carrier of a genetic information-DNA- is a polymer consisting of four monomers nucleotides. They are denoted usually as A, T, G and C. The sequence of their position in the DNA polymeric chain defines the information coded in genes and in the entire genome. Genomes of different organisms contain several millions to several billions of nucleotides. With the existing procedure in the entire world during one year there are sequenced genome regions of only 1 million nucleotides length. Consequently, for decoding of, for example, a human genome of 3 billion nucleotides, the time required will take 3,000 years. Therefore, to solve the problem of sequencing of whole genomes within real time limits and with real expenditures, it is necessary, first of all, to have high-speed automated and relatively inexpensive devices operating on principally new technologies.

Sequencing of DNA or RNA involves a number of stages the most crucial of which is the stage of an electrophoretic determination of the primary structure of nucleic acids. The main problems of this stage originating upon shifting towards a largescale sequencing are caused mainly by limited possibilities of improving the method productivity, a low accuracy and sophisticated character of the employed measurement devices.

Known in the art is a process for an electrophoretic determination of the primary structure of nucleic acids (J. Hindley, "DNA sequencing" in "Laboratory techniques in biochemistry and molecular biology", vol. 10, 1983, Elsevier biomedical press, Amst., N.Y., Oxford, p. 78–83) which comprises placing samples of a nucelic acid in the form of fragments of regions of its polymeric chain containing radioactive tags onto a layer of a gel in the form of a vertically placed plate on the upper end face thereof. The creation of the gel layer is effected by polymerization thereof from a solution of monomers poured into a cuvette. The cuvette is made as two glass plates between which two gaskets are placed whose thickness dictates the gel layer thickness, usually 0.25–0.35 mm. A sealing film is used for assembling the cuvette. Prior to polymerization of the gel layer the surface of one of the plates is treated with a solution imparting hydrophobic properties thereto, whereafter the cuvette is assembled in such a way that the treated surface be directed inside the cuvette.

An electrical potential is then applied to the gel layer which causes a electrophoretic separation of the fragments along the gel layer height in accordance with the fragment size which defines their mobility. When the smallest of the fragments reaches the lower end of the gel which is determined by the position of a dye introduced together with the samples and having an electrophoretic mobility equal to the mobility of the smallest of the fragments, the electric potential is switched-off. Then the cuvette is dissembled and the treated plate is removed. The gel layer remaining on the second plate is dried and an X-ray film is applied onto it to record the radioactivity of the bands of the separated fragments. The exposure is effected for a period of 1 to 3 days. Then the film is developed. The position of darkened bands on the film is used to assess the sequence of nucelotides in the molecules of the analyzed nucleic acid.

Known in the art is an apparatus for carrying out the process for an electrophoretic determination of the primary structure of nucleic acids (J. Hindley, "DNA sequencing" in "Laboratory techniques in biochemistry and molecular biology" vol. 10, 1983, Elsevier biomedical press, Amst., N.Y., Oxford, p. 78–83) comprising a vertically mounted cuvette for placing a gel layer with samples of an nucleic acid. The cuvette is made in the form of a rectangular chamber formed by two polished glass plate with two gaskets. The plates are fixed to each other by means of an adhesive tape. To form a recesses in the gel layer to introduce samples thereinto, the chamber is provided with means for forming the recesses.

The apparatus also has chambers with electrode solutions fixed in the upper and lower parts of the cuvette and embodied so that the solutions are communicating with the cuvette. In the chambers with the electrode solutions there are electrodes connected to a current source.

For recording the results of the electrophoretic separation the apparatus is provided with an X-ray film.

In the above-described process a number of operations such as assembling of the cuvette, placing of the gel layer in the cuvette which is effected by way of pouring thereinto of a solution of monomers, dissembling of the curvette and preparation of the gel layer to autoradiography are very labour consuming which makes the process low in productivity. Furthermore, these operations necessitate high professional skill of the operator. For example, upon pouring of the monomer solution into the cuvette the formation of air bubbles in the gel layer is possible which causes a considerable distortion of the electric field lines in the gel and hinders interpretation of the results of separation, while upon separation (detachment) of the plate during the dissembling of the cuvette after electrophoresis for the gel autoradiography the gel layer might be damaged which causes losses of a part or even all of the results of the analysis. This also lowers the process productivity.

The above-described process features a long-time recording lasting for 1–3 days. This substantially limits the process productivity, especially in the cases where all the subsequent operations should be carried out with the account of the preceding ones, for example in experiments for the determination of the primary structure of nucleic acids.

The reason of this resides in the use of a radioactive tag which causes a long-time autoradiographic process of recording. Furthermore, the use of a radioactive tag defines instability of the tagged compounds employed in the sequencing, as well as a lower, than in the gel, resolution of the bands, since their width in the gel is smaller than in the X-ray film after the autoradiography.

The above-mentioned disadvantages are also inherent in an apparatus for practicing this method and are caused mainly by the cuvette design. Apart from difficulties of placing the gel therein and preparation of the cuvette for the autoradiography, it design is responsible for the gel temperature non-uniformity from sample to sample due to a non-uniform heat-removal in the middle portion of the cuvette and on its periphery. This results in a considerable distortion of the bands and in errors in interpretation of the results.

Also known in the art is a method for an electrophoretic determination of the primary structure of nucleic acids (GB, A, 2155176) comprising placing samples of a nucleic acid in the formof fragments of its polymeric chain regions containing fluorescent tags of different spectra onto a gel—a vertically positioned column, on the upper end thereof. The gel is obtained by polymerization from a solution of monomers in a cylindrically-shaped cuvette made from an optically transparent material. An electrical potential is applied to the gel layer for an electrophoretic separation of the fragments in the direction of passage of electric current, i.e. along the gel column height, according to their size. The fragments are recorded by each of the fluorescent tags to establish a relative position of the fragments in the gel colunm which is used to determine the sequence of nucleotides in the molecule of the analyzed nucleic acid.

In the prior art process discussed hereinabove use in made of four different fluorescent tags differing in both excitation spectra and in emission spectra which enables a separate recording thereof.

Known in the art is an apparatus for performing the process for an electrophoretic determination of the primary structure of nucelic acid (GB, A, 2155176) which comprises a vertically mounted cylindrically-shaped cuvettee made from a dielectric material to place a gel with samples of a nucleic acid having in its upper and lower parts chambers with electrode solutions, wherein electrodes are positioned which are connected to a source of current and are communicating with the cuvette to effectuate an electric contact of the electrode solutions with the gel. The apparatus also has a source of a monochromatic radiation with its light beam directed, through a system of four excitation filters rigidly connected therebetween and provided with a drive for moving thereof to align any of the filters with the optical axis of the source, to a region of the cuvette positioned in its lower part. While passing through the filter, the light beam in the range of wavelengths set by this filter and corresponding to the excitation spectrum of a particular fluorescent tag causes a fluorescent radiation.

The apparatus also has a system of removable emission filters rigidly connected therebetween and provided with a drive for moving them to put this or other emission filter onto the optical axis of a receiver of the fluorescent radiation from the tags at an angle within the range of from 0° to 90° to the optical axis of the monochromatic radiation source. The sensor of the receiver of the fluorescent radiation from the tags faces the region of the gel illuminated by the monochromatic radiation source. The apparatus is also provided with a sensor of the position of the filters to control operation of both systems of the filters. The sensor of the filter position is connected to the address input of the recording unit and the fluorescent radiation reciver-to the information input of the recording unit. During the recording one of the four channels of the recording unit is commutated to the information input. The selection of the channel is effected by the address which is obtained as a signal from the sensor of the filter position.

Owing to the use of fluorescent tags the above-described process and apparatus enable elimination of a number of labour-consuming operations (disassembling of the cuvette, preparation of the gel for autoradiography) inherent in the prior art method and apparatus. Furthermore, these tags are stable and in their recording no deterioration of the resolution occurs in the gel. The main advantage of the process and apparatus discussed hereinabove resides in a considerable, by 3 to 5 times, increase in their productivity owing to elimination of lengthy process of autoradiography.

However, a number of factors hinders interpretation of the results of an electrophoretic determination of the primary structure of nucleic acids carried out with the use of four fluorescent tags. The first disadvantage resides in that the emission spectra from different tags are overlapping to a considerable extent. As a result, the signals from one tag are present in more than one channel of the recording unit in its receiver of the fluoroescent radiation. Therefore, it is necessary to determine the quantitative content of the four tags present in the gel at any given moment of time. The second important factor complicating the process is defined in that the molecules of different fluorescent tags have different electrophoretic mobility. Consequently, also variable is the mobility of the fragments labeled by various fluorophors which results in an impaired resolution of the bands of the fragment and, hence, in the presence of an essential error in determination of the sequence of nucleotides of nucelic acids. The third factor is connected with essential variations of the number of fragments of a particular size for each of the reactions of their synthesis in preparation of samples which tells upon the intensity of the bands in the gel and, with the account of the first factor, still more complicates the analysis of the data obtained. All this causes the necessity of using sophsticated computer programs for processing the results o fthe analysis by the electrophoretic method the use of which makes it possible to minimize the error in determination of the sequence of nucelotides in nucleic acids only to 1% which is insufficient for such method as sequencing.

Though the above-described method and apparatus improve the analysis productivity as compared to the radioisotope method, it is either insufficient and a further improvement of the productivity is difficult for the following reasons. In a gel column it is possible to simultaneously analyze four samples. If the method makes use of a gel plate as that realized in an apparatus disclosed in the paper by J. M. Prober et al. "A system for rapid DNA sequencing with fluorescent chainterminating dideoxynucleotides", vol. 238, 1987, Science, pp. 336–341" the number of simultaneously analyzed samples can be brought to 48. However, a limit exists here as well which is determined by the use of a special scanning photomultiplier as a receiver of a fluorescent radiation.

The use of four fluorescent tags necessitates the availability of sophisticated instruments for recording of their spectra and rather complicated programs for processing of the obtained results. This complexity is even higher with the necessity of increasing the process productivity. Thus, in the apparatus disclosed in this reference two expensive scanning photomultipliers are employed along with a great number of expensive large-size interference filters.

SUMMARY OF THE INVENTION

It is an object of the present invention to provide a process for an electrophoretic determination of the primary structure of nucleic acids making it possible to increase, by more than an order of magnitude, the productivity of determination of the primary structure of nucleic acids and to lower, also by an order of magnitude, the error in the determination of the sequence of nucleotides of nucleic acids.

It is another object of the present invention to provide an apparatus for an electrophoretic determination of the primary structure of nucelic acids which would make it possible to increase, by an order of magnitude, the productivity of determination of the primary structure of nucelic acids; to lower, by an order to magnitude, the error in determination of the sequence of nucelotides of nucelic acids and to simplify its design.

This object is accomplished by providing a process for the electrophorectic determination of the primary structure of nucelic acids wherein in that samples of a nucleic acid in the form of fragments of its polymeric chain containing tags are placed onto a gel, to which an electric potential is applied for an electrophoretic separation of the fragments in the direction of passage of electric current in accordance with their size and the fragments are recorded by their tags to establish their relative position in the gel to judge about the sequence of nucelotides in a molecule of a nucelic acid. In accordance with the present invention the gel is shaped as a hollow cylinder, samples of the nucelic acid are placed in recesses which are located at its end face around the circumference; the voltage for an electrophoretic separation of fragments in the direction of passage of electric current in accordance with their size is applied to the end faces of the hollow cylinder, the cylindrically-shaped gel is kept at a constant temperature at a level at which the movement of the fragments of the nucleic acid polymeric chain is effected without their chemical combination at hydrogen bonds by means of a layer of a non-polar liquid through control of its temperature, this layer being located on one of the side surfaces of the hollow cylinder and its height is selected to be approximately equal to the height if the hollow cylinder, and the recording of the fragments of regions of the nucelic acid polymeric chain is effected by rotating the gel shaped as a hollow cylinder around the axis thereof.

It is advisable that in the process for an electrophoretic determination of the primary structure of nucleic acids according to the present invention the gel shaped as a hollow cylinder would have different porosity in its individual regions and at least two samples of a nucleic acid containing the same fragments of the same regions of the polymeric chain be taken and placed onto the regions of the gel shaped as a hollow cylinder which regions have different porosity.

It is also advisable that in the process of an electrophoretic determination of the primary structure of nucleic acids, in accordance with the present invention, between the gel shaped as a hollow cylinder and the non-polar liquid layer be positioned a layer of a polymeric material resistant to the non-polar liquid.

This object is also accomplished by providing an apparatus for an electrophoretic determination of the primary structure of nucleic acids comprising a vertically-mounted cylindrically-shaped cuvette of a dielectric material to contain a gel with samples of a nucleic acid having, in its upper and lower parts, chambers with electrode solutions, wherein electrodes are provided which are connected to a source of current and communicating with the cuvette to effect an electric contact of the electrode solutions with the gel; a source of monochromatic radiation with its light beam being directed to a region of the cuvette located in its lower part and exciting in samples of the nucleic acid a fluorescent radiation from the tags of fragments of regions of its polymeric chain, and a receiver of the tag fluorescent radiation with its sensor facing the gel region illuminated by the monochromatic radiation source and connected to the information input of a recording unit onto the address input of which signals corresponding to the sample number are fed; in accordance with the present invention the cuvette is shaped as a sleeve provided with a drive for rotation around its axis and mounted on a platform, and a sensor of the turn angle with its output connected to the address input of the recording unit; the chambers are formed by the lateral wall and bottom of this sleeve, as well as by the side wall and bottom of an additional sleeve from a dielectric material mounted coaxially with the main sleeve and secured to the platform; a means is also provided to maintain a constant temperature of the gel which means contains a non-polar liquid located between the electrode solutions in the region between the side walls of the main and additional sleeves and a heat-exchanger placed in the non-polar liquid; the electrode solution located under the non-polar liquid has a higher density than the non-polar liquid and the electrode solution located above it—a lower density; the electrodes have a annular shape and are positioned coaxially with the main and additional sleeves and are rigidly connected with the additional sleeve.

Owing to the radial symmetry in the gel arrangement and that of annular electrodes and means for maintaining constant temperature of the gel and to selection of the direction of electrophoresis along the generatrix of the hollow cylinder, there are ensured the conditions for separation of the analyzed molecules identical for all the tracks. This results in a minimized error in the determination of the sequence of nucleotides of nucleic acids.

Rotation of the cuvette shaped as a sleeve around its axis during electrophoresis which is effected for recording the components of samples of the nucleic acid ensures at the same time a uniform and continuous stirring of both the electrode solutions and of the non-polar liquid which also contributes to reduction of the error in teh determination of the sequence of nucleotides owing to maintaining a uniform composition of the electrode solutions, the removal of the gas bubbles from the electrodes and improvement of the heat-transfer conditions in the non-polar liquid.

The gel movement relative to the light beam from the monochromatic radiation source effected by rotation of the sleeve ensures a simple way of scanning the gel, since in practice it is more easily to effectuate a rotative motion than a reciprocal one and the accuracy of the former is higher than that of the latter. Consequently, the error is also diminished due to specific features fo recording of the components of the analyzed samples. At the same time, the apparatus design is also simplified.

Due to a better contact of the heat-transfer agent, which is the non-polar liquid, with the gel, as well as due to stirring of the heat-transfer agent it is possible to determine the primary structure of nucleic acids at a maximum possible speed without risking the gel overheating in electrophoresis and, hence, there is an opportunity for an additional improvement of productivity of the process and apparatus.

In the apparatus according to the present invention no vessels for the electrode solutions are employed. Their role is taken by the main and additonal sleeves, whereby the apparatus design is simplified.

It is advisable that in the apparatus according to the present invention for an electrophoretic determination of the primary structure of nucleic acids the monochromatic radiation source be mounted so that its light beam be directed to the bottom of the main or additional sleeve which bottom would made from a material optically transparent for the monochromatic radiation.

It is advantageous that in the apparatus for an electrophoretic determination of the primary structure of nucleic acids according to the present invention there would be provided a means for the formation of a gel from solutions of monomers in the shape of a hollow cylinder which is represented by the main sleeve with a drive for rotation thereof around its axis and a means for the formation of recesses on the end face of the hollow cylinder which has an annular insert provided in the upper part of the main sleeve and having longitudinal grooves on its external cylindrical surface which form slots between the annular insert and the inner surface of the side wall of the main sleeve; an annular insert with projections made on its end face along the perimeter thereof which are positioned in the slots; a sealing ring provided over the annular insert with the projections and a lid with an opening mounted on the end face of the main sleeve.

This makes it possible to shape the gel as a hollow cylinder and thus to ensure the required conditions for increasing productivity, lowering the error in the determination of the sequence of nucleotides and simplifying the apparatus design. The error reduction is also attained owing to identical conditions necessary for the production of a uniform gel, due to elimination of the probability of the formation of gas bubbles in the gel which are removed from the solution under the effect of the centrifugal force and due to the presence fo slots for introduction of samples and of availability of an annular insert with projections ensuring the formation of similar and geometrically regular initial regions of the gel.

It is advisable that in the apparatus for an electrophorectic determination of the primary structure of nucleic acids according to the present invention the platform be rotatably mounted with the possibility of being turned to 90° in the vertical plane and be provide with fixing members in its extreme positions.

This ensures the production of a uniform thickness of the gel along the generatrix of the cylindrical sleeve and, hence, lowers the error in determination of the sequence of nucleotides.

It is also advisable that in the apparatus for an electrophoretic determination of the primary structure of nucleic acids according to the present invention the inner surface of the side wall of the main sleeve would have the shape of a tapered cone with its greater base facing the bottom of the main sleeve.

Owing to this arrangement it is possible to produce the gel in the form of a hollow cylinder having its wall thickness in the cross-section uniformly incresing from the starting zone in the direction of migration of molecules. This results in a gradual reduction of the current density in this direction, thus contributing to a levelling of the resolution for both long and short polymer chains of the nucleic acid. In this manner the error in the determination of the sequence of nucleotides is also lowered.

It is desirable that in the apparatus for an electrophoretic determination of the primary structure of nucleic acid according to the present invention on the inner surface of the side wall of the main sleeve along the generatrix from the sleeve bottom to the region of the annular insert with longitudinal grooves projections be provided which would be uniformly positioned along the circumference.

It is also advisable that in the apparatus according to the present invention for an electrophoretic determination of the primary structure of nucleic acids the projections on the inner surface of the side wall of the main sleeve in their cross-section be of a T-like shape.

It is desirable that the apparatus for an electrophoretic determination of the primary structure of nucleic acid according to the present invention contain an annular chamber having a trapezoidal form in its cross-section with radial partitions according to the number of projections on the inner surface of the side wall of the main sleeve positioned uniformly along its circumference and forming cavities for containing solutions of monomers, said chamber being positioned under the annular insert with the longitudinal grooves and rigidly connected with the lid and facing it with the greater base of the trapezoid; in the upper part of the external side wall of said annular chamber openings should be provided for outflowing of solutions of monomers onto corresponding regions of the inner surface of the side wall of the main sleeve limited by the projections.

This enables the formation, in the same sleeve, a gel in the shape of a hollow cylinder having different porosity at different regions (different concentrations of acrylamide) positioned along the circumference and, hence, producing a different "rectention" effect on low-molecular and high-molecular fragments of the analyzed samples. This enables lowering of the error in the determination of the seqence of nucleotides. The possiblilty of carrying out this in the same cuvette and during the same process ensures a higher productivity and simplification of the apparatus. At the same time, the use of a gel with different concentrations of acrylamide in different regions for the same sample makes it possible to shorten the process duration, since high-molecular fragments can be recorded in the regions with a low content of acrylamide, wherein their mobility is higher than in the regions with a low porosity. At the same time, the required resolution of low-molecular fragments of the sample is ensured within the same time period in the region with a high content of acrylamide. Therefore, owing to a reduced time of determination of the primary structure there is ensured an increased productivity of the process.

BRIEF DESCRIPTION OF THE DRAWINGS

The present invention is further illustrated by the description of its particular embodiments with reference to the accompanying drawings, wherein:

FIG. 3 is a general view of the means for the formation of a gel from a solution of monomers shaped as a hollow cylinder (partial elevation view) according to the present invention;

FIG. 4—a cross-section along the line IV—IV in FIG. 3;

FIG. 6—a cross-section along the line VI—VI in FIG. 3;

DETAILED DESCRIPTION OF THE INVENTION

Figure 1:
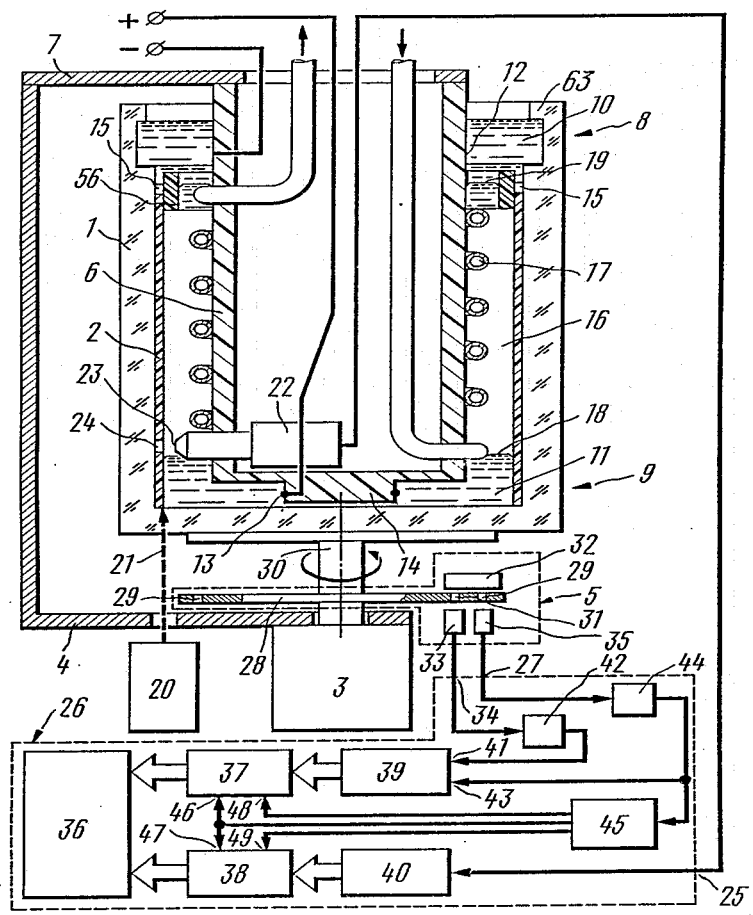
FIG. 1 is a general view of an apparatus for the electrophoretic determination of the primary structure of nucleic acids (elevation section) adn a blockscheme of its recording unit according to the present invention.

The process for the electrophoretic determination of the primary structure of nucleic acids of DNA or RNA comprises preparation of samples in the form of tagged fragments of regions of its polymeric chain and an electrophoretic analysis of these fragments. One of the most popular methods for the preparation of DNA samples is the method of termination of the reaction of polymerase copying (Sanger method) wherein tagged DNA fragments are obtained by their synthesis in an analyzed DNA region as in a matrix. This region is preliminarily multiplied by cloning in a system of a bacteriphage having a single-chain DNA, e.g. M13 bacteriophage. Thereafter, there is effected a complementary binding of a short oligonucleotide primer with a region of the phage DNA directly adjacent to the built-in region of the DNA. Owing thereto, the synthesis of each fragment effected as building-up of the primer in the direction of the analyzed DNA region from the 3'-terminal towards the 5'-terminal is started from the same point in the DNA-matrix. To introduce a tag into each fragment, use is made of a primer M13 fluorescently tagged at the 5'-terminal. As the fluorescent tag use is made of, for example, tetramethylrhodamine having a maximum in its excitation spectrum at 560 nm and maximum in its emission spectrum at 575 nm.

In fact, each DNA fragment is only a complementary replica of the analyzed DNA region. However, due to the rule of the complementary interaction: A is complementary to T, and G- to C, it is not difficult to establish the sequence of nucleotides of the analyzed DNA region by the structure of the fragments.

To obtain fragments of different length with an interval of one nucleotide, the synthesis is conducted in the presence of nucleotide analogs. The incorporation of one nucleotide analog into the polymeric chain of the fragment being synthesized results in termination of its growth. Four individual reaction mixtures are prepared, each of them containing only one nucleotide analog, i.e. either analog A, or T, or G, or C. As a result of the reaction of synthesis, in one mixture there are obtained fragments terminating only with A, in another—only with T, and so on and in the four reaction mixtures on completion of the reaction there are present fragments of each size possible for the given DNA region. The preparation of samples is completed by their denaturation which results in separation of polymeric chains of the DNA-matrix and the fragments incorporating the tagged primer.

The preparation of samples for an electrophoretic determination of the primary structure of DNA by another popular method (Maxum and Gilbert method) comprises a chemical treatment of molecules of a particular region of a nucleic acid to obtain different-size fragments of this region similar to those which are obtained by the Sanger method. In so doing, a tag is introduced into the molecules either at the 3'-terminal or at the 5'-terminal. The fragments are obtained, likewise in the Sanger method, in four reactions and, hence, fed for analysis are also four samples from each analyzed region of the nucleic acid. The preparation of RNA samples is effected by a method similar to the Maxam and Gilber method.

The thus-prepared samples of a nucleic acid, in the form of fragments of regions of its polymeric chain, containing the tags are placed onto a gel in the form of a hollow cylinder by introduction into recesses which are positioned in a circle on its end face. Each sample comprising an individual reaction mixture (in respect of A, T, G and C) is introduced into a separate recess and a particular sequence of introduction of samples is followed, e.g. ATGC or ACGT for all the introduced samples.

The gel is prepared either by polymerization from a solution of monomers, or use is made of ready plates (Akiyoshi Wada, "Automated high-speed DNA sequencing", Nature, vol. 325, 1987, p.771-772), comprising a layer of a polyacrylamide gel coated on two sides with a polymeric film. On one side of such a plate in the gel layer there are made rectangular recesses for introducing samples. For sequencing use is usually made of a polyacrylamide gel which is obtained by polymerization of the solution containing the monomers: acrylamide and methylenebisacrylamide, as well as additives initiating the reaction of polymerization: tetramethylethylenediamine and ammonium persulphate. Upon polymerization of the gel in the form of a hollow cylinder rectangular recesses are made on one of its end faces for placing samples of nucleic acid samples thereinto. In the case of using ready plates of the gel, they are placed so that the recesses be positioned in a circle on one of the end faces of the hollow cylinder made by bending a gel plate till its opposite ends contact each other.

For an electrophoretic separation of DNA fragments in the direction of passage of electric current according to their size, an electromotive potential difference is applied to the end faces of the hollow cylinders through the electrode solutions wetting both end faces. On one of the side surfaces of the hollow cylinder a layer of a non-polar liquid is located to maintain a constant temperature of the gel layer at a level at which the movement of fragments of a polymeric chain of a nucleic acid is effected without their chemical combination at hydrogen bonds. The temperature of the non-polar liquid is subject to control in this case. As the non-polar liquid use is made, for example, of a mixture of hexane and carbon tetrachloride with a density of $1.06 \pm 0.02$ g/cm$^3$. The layer thickness of the non-polar liquid is selected approximately equal to, or, more exactly, slightly lesser than the height of the hollow cylinder.

In the electrophoretic separation the fragments having the same size defined by the number of nucleotides incorporated therein are moving along the height of the hollow cylinder in the form of a uniform zone comprising a band. Under the influence of electric current and different braking of fragments of a different size in the pores formed by a spatial structure of the polyacrylamide gel there occurs an electrophoretic separation of the fragments. The highest resolution is attained at the end face of the hollow cylinder opposite to the spot of application of samples and at that very end face the recording of the fragments, i.e. of the bands is effected.

The recording of fragments of regions of the polymeric chain of the nucleic acid is effected by rotating the gel shaped as a hollow cylinder around its axis. In so doing, recorded is the fluorescent radiation of the bands of each sample upon the movement of the fragments along the height of the hollow cylinder. The sequence of signals obtained as a result of recording of the fluorescent radiation at a known arrangement of each of the four reaction mixtures in the recesses is adequate to the sequence of the four nucleotides (A, T, G, C) in the analyzed DNA region.

The concentration of acrylamide in the gel defines its porosity. If it is equal, for example, to 10% by weight, in the layer of such gel it is possible to separate fragments of 50 to 200 nucleotides length. Since one of the main limitations of the process for an electrophoretic determination of the primary structure of nucleic acids resides in its resolving power, it is frequently preferred to change the gel porosity depending on the size of the analyzed DNA region. For example, a gel with the concentration of acrylamide of 6% makes it possible to separate fragments having length of more than 250 nucleotides.

To improve the resolving power of the process for an electrophoretic determination of the primary structure, the gel shaped as a hollow cylinder is made with a different porosity in individual regions located around its circumference. In the case where such regions number two and over, the gel shaped as a hollow cylinder consists of two or more bent plates. In this case use is made of at least two samples of a nucleic acid containing the same (either in respect of A, or T, and so on) fragments of the same regions of its polymeric chain and they are placed into recesses made on different plates having, accordingly, different porosity. In other words, each reaction mixture is separated, for example, into two portions one of which is introduced into a recess of a region with a greater porosity and the other portion—into a recess of a region with a smaller porosity.

As the non-polar liquid, apart from the mixture of hexane and carbon tetrachloride, use can be made of other mixtures or one liquid of the required density. However, these liquids can produce a negative effect on the gel or on the fragments being analyzed. To prevent this and to use such a non-polar liquid which ensures the best heat-transfer conditions, between the gel shaped as a hollow cylinder and the layer of the non-polar liquid there is positioned a layer of a polymeric material resistant in respect of the non-polar liquid. As such material use can be made, for example, of polytetrafluoroethylene.

The apparatus for an electrophoretic determination of the primary structure of nucleic acids by the process according to the present invention comprises a vertically mounted cuvette shaped as a sleeve 1 (FIG. 1) from a dielectric material such as polystyrene or polymethylmethacrylate. It is possible that it is made from two sleeves tightly connected with each other: an outside sleeve from titanium or an aluminium alloy and an inside sleeve from polymethylmethacrylate or polystyrene. On the inner surface of the side wall of the sleeve 1 a gel 2 shaped as a hollow cylinder is located. The sleeve 1 is provided with a drive 3 for rotation thereof around its axis and mounted on a platform 4, as well as with a sensor 5 of the turn angle. An additional sleeve 6 from a dielectric material such as polymethylmethacrylate is coaxially mounted relative to the sleeve 1; in the discussed embodiment it is mounted inside the sleeve 1. The sleeve 6 is fixed on a cantilever 7 mounted on the platform 4. In the upper and lower parts of the sleeve 1 there are chambers 8 and 9 with electrode solutions 10 and 11. The chamber 8 is formed by lateral walls of the sleeves 1 and 6 and the chamber 9— by side walls and the bottom of these sleeves 1 and 6. In the solutions 10 and 11 there are annular electrodes 12 and 13 made from platinum. The annular electrodes 12 and 13 are secured on the sleeve 6 and positioned coaxially therewith. The annular electrode 12 is secured on the external surface of the side wall of the sleeve 6 in its upper part and the annular electrode 13—on the external cylindrical projection 14 made on the bottom of the sleeve 6. The annular electrodes 12 and 13 are connected to a current source.

In the gel 2 shaped as a hollow cylinder along the circumference of its end face there are provided recesses 15 wherein samples of a nucleic acid are placed. Under the influence of electric current passing through the gel in the direction from one end face of the hollow cylinder to the other the components of the analyzed samples migrate to the lower part of the gel 2 forming tracks of the bands where their recording is effected.

The apparatus also has a means for maintaining a constant temperature of the gel heating upon passing of electric current therethrough; this means consists of a non-polar liquid 16 located between the electrode solutions 10 and 11 in the region between the side walls of the sleeves 1 and 6, as well as of a heat-exchanger 17 immersed into the non-polar liquid and made from a helically wound polytetrafluoroethylene tube connected to a water thermostating unit (not shown) by means of outlet socket pipes. The arrows show the direction of water flow through the heat-exchanger 17. The electrode solution 11 has the density of $1.100\pm0.015$ g/cm$^3$ which is ensured due to the presence of saccharose therein, the solution 10 has the density of about 1.00 g/cm$^3$. Therefore, the non-polar liquid 16 having, as it has been already mentioned hereinbefore, the density of $1.06\pm0.02$ g/cm$^3$ is positioned between the electrode solutions 10 and 11. The boundaries of the interface of the liquids are shown in the drawing by lines 18 and 19.

For recording the components, tagged with a fluorophor, of samples of a nucleic acid the apparatus is provided with a source 20 of a monochromatic radiation such as an argon laser with its light beam directed to the lower part of the sleeve 1 and it excites a fluorescent radiation in the fragments tagged with the fluorophor. This radiation is detected by a receiver 22 of the fluorescent radiation from the tags which is provided in the lower part of the sleeve 6 so that its sensor faces the region 24 of the gel 2 illuminated by the source 20. The receiver 22 is connected to the information input 25 of the recording unit 26 to the address input of which the sensor 5 of the turn angle of the sleeve is connected.

In the disclosed embodiment the sensor 5 has a disk 28 with an number of openings 29 equally spaced from the centre the number of which is equal to the number of recesses 15 of the hollow cylinder and the angular distance between them is equal to that between the recesses 15. The disk 28 is fixed on a shaft 30 of the drive 3. Furthermore, still another opening 31 is provided in the disk 28 which is located between two openings 29 corresponding to the first and the last recess 15, but at a smaller distance from the centre of the disk 28. The sensor 5 has a light diode unit 32 positioned opposite to the openings 29 and 31 and two photodiodes: the base one 33 connected to the input 34 of the recording unit 26 and the computation diode 35 connected to the address input 27.

The recording unit 26 has a memory unit 36 connected by means for the address bar to the address register 37 and by means of the data bar—to the data register 38. In turn, the register 37 is connected by means of a bar to a counter 39 and the data register 38—to the output of the analog-to-digital converter 40. The input of the analog-to-digital converter 40. The input of the analog-to-digital converter 40 is connected to the information input 25 of the recording unit 26. The setting input 41 of the counter 39 is connected, through a pulse-forming unit 42, to the input 34 and the computation input 43 of the counter 39 is connected, through a pulse-forming unit 44, to the address input 27 of the recording unit 26. The recording unit 26 also has a generator 45 of pulses of reading and set-off with its input connected to the output of the pulse-former 44 and the outputs—to the reading inputs 46 and 47 and zero-setting inputs 48 and 49 of the registers 37 and 38.

Figure 2:
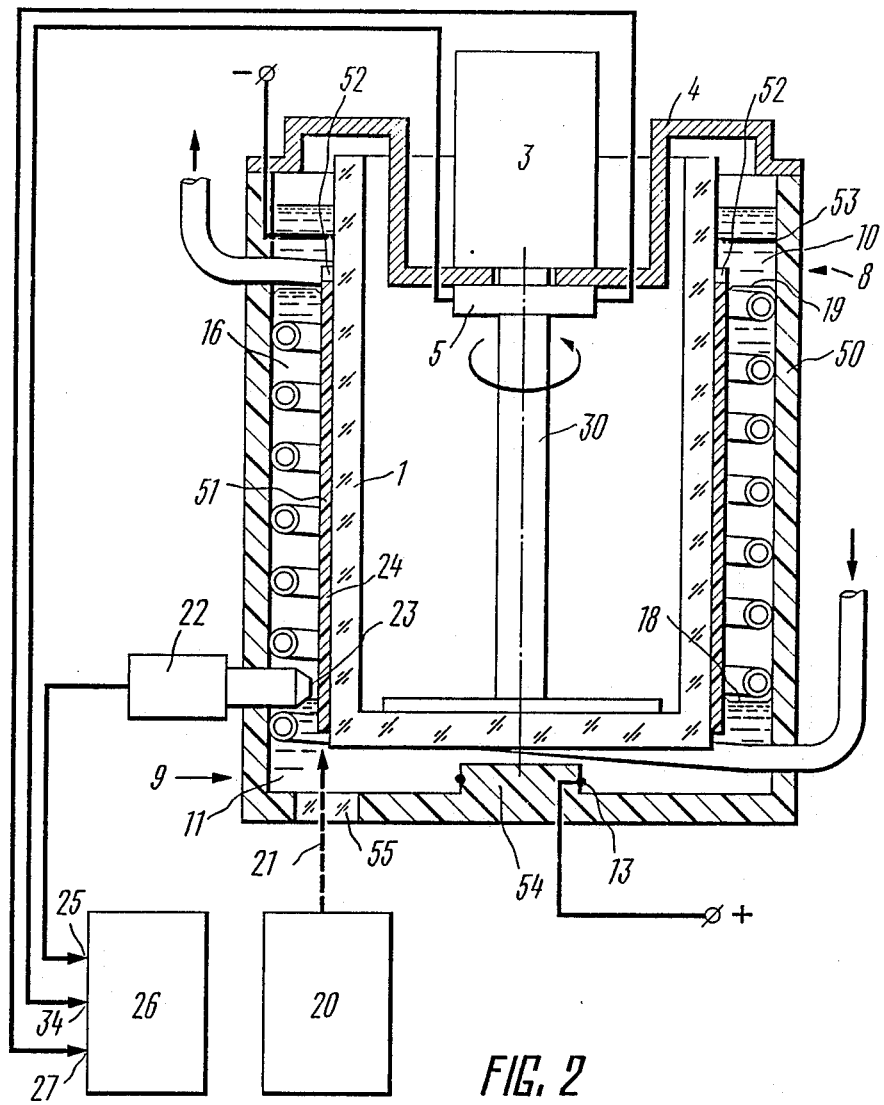
FIG. 2 is a general view of an apparatus for the electrophoretic determination of the primary structure of nucleic acids in an embodiment, wherein the gel is located on the external surface of a sleeve (elevation view) according to the present invention.

In the disclosed embodiment of the apparatus according to the present invention the gel 2 in the form of a hollow cylinder is located on the inner surface of the side wall of the sleeve 1. Another embodiment of the apparatus according to the present invention is possible, wherein the gel is located on the external surface of the side wall of the sleeve 1 (FIG. 2). In this case the sleeve 1 is mounted inside an additional sleeve 50 coaxially therewith and the gel 51 shaped as a hollow cylinder is produced by bending a ready gel plate or plates with preformed recesses 52 to contain samples, e.g. the above-described gel plate coated on its both sides with a polymeric film. The plates are fixed on the lateral surface of the sleeve 1 by means of soft spring rings (not shown). The gel plates are positioned so that recesses 52 are arranged in a circle in the upper part of the sleeve 1. The annular electrode 53 in this embodiment is mounted on the inner surface of the side wall of the additional sleeve 50 coaxially therewith and the annular electrode 13—on the inner cylindrical projection 54. A window 55 of a light-permeable material is provided in the bottom of the additional sleeve 50 to pass the light beam from the source 20.

Figure 5:
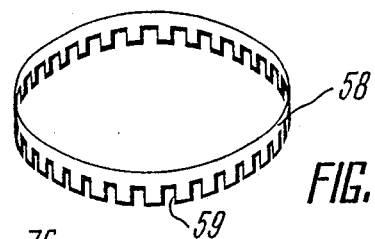
FIG. 5—a general view of the annular insert with the projections made on its end face along the circumference (isometry) according to the present invention.

When the gel 2 is placed on the inner surface of the side wall of the sleeve 1 (FIG. 1) by way of pouring thereinto a solution of monomers forming a gel upon polymerization, the apparatus has a means for the formation of the gel 2 from a solution of monomers in the shape of a hollow cylinder which is represented by the main sleeve 1 with the drive 3 for rotation thereof around its axis and a means for the formation of recesses 15 on the end face of the hollow cylinder. The latter means has an annular insert 56 (FIGS. 3 and 4) placed in the upper part of the sleeve 1 and made from polymethylmethacrylate with longitudinal grooves 57 provided on its external cylindrical surface and forming slots between the annular insert 56 (FIG. 3) and the inner surface of the side wall of the main sleeve 1, an annular insert 58 with projections 59 (FIG. 5) provided at its end face in a circle which are engaged in the slots, a sealing ring 60 (FIG. 3) provided over the annular insert 58 and a lid 61 with a hole 62. The lid 61 is secured by means of fixing members (not shown) to the projections 63 on the end face of the sleeve 1. The hole 62 is intended for pouring of the solution of monomers.

The platform 4 is mounted pivotably to be turned to the angle of 90° in the vertical plane. To this end, it is mounted on a shaft 64 of a drive 65 and is provided with fixing members 66 and 67 of the extreme positions of the platform 4 which are provided on a base which is common for the drive 65: the fixing member 66 is intended for fixation of the platform 4 in the vertical position and the fixing member 67—in its horizontal position.

On the inner surface of the side wall of the main sleeve 1 along the generatrix from the bottom of the sleeve 1 to the region of fixation of the annular insert 56 projections 68 are provided which are uniformly arranged in a circle. The projections 68 are made, for example, from polymethylmethacrylate and have a T-like shape in their cross-section (FIG. 6).

Upon the formation of the gel as a hollow cylinder containing regions with different porosity, the apparatus has an annular chamber 69 (FIGS. 7 and 8) from polymethylmethacrylate which consists of a housing 70 and a lid 71 and has a trapezoidal form in its cross-section with radial partitions 72 according to the number of projections 68 positioned uniformly in circle and forming cavities 73 (FIG. 8) for containing solutions of the monomers. The annular chamber 69 is located under the annular insert 56 (FIG. 7) and is fixed on a lid 74 by means of legs 75. In this case the greater base of the trapezium faces the lid 74. To introduce solutions of monomers into the cavities 73, openings 76 are provided in the lid 74 according to the number of the cavities 73. In the upper part of the external side wall of the annular chamber 69 at the point of junction of the housing 70 and the lid 71 holes 77 of a square form are provided for outflow of the solutions of the monomers onto corresponding regions of the inner surface of the side wall of the sleeve 1 which are limited by the projections 68, upon rotation of the sleeve 1.

The embodiment of the sleeve 1 (FIG. 1), wherein the inner surface of its side wall has a form of a tapered cone facing with its greater base the bottom of the sleeve 1 is not shown in the drawing, since the conicity in this embodiment is about 0.07 of an angular degree or 0.001 radian.

In the apparatus according to the present invention the source 20 of the monochromatic radiation is mounted so that its light beam 21 is directed to the bottom of the sleeve 1 or the sleeve 50 (FIG. 2). The bottom of the sleeve 50 is provided with a window 55 for passing the light beam 21.

The principle of operation of the apparatus for an electrophoretic determination of the primary structure of nucleic acids according to the present invention is further illustrated by the description of its several embodiments.

Thus, upon the formation of a gel as a hollow cylinder directly in the sleeve 1 (FIG. 3) into this sleeve at the energized fixing member 66 intended for fixation of the platform 4 in the vertical position the annular insert 56 is placed till its lower end face contacts the projections 68 provided on the inner surface of the side wall of the sleeve 1 and into the slots formed by the longitudinal grooves 57 the annular insert 58 is placed, whereafter inserted are the sealing ring 60 and the lid 61. The latter is fixed in the sleeve 1 by means of fixing members to the projection 63 thus ensuring a tight contact of the sealing ring 60 with the sleeve 1.

Through the opening 62 in the lid 61 a tube is inserted down to the bottom of the sleeve 1 which communicates with a source of an inert gas (not shown) for the supply of the inert gas into the sleeve 1 and the latter is filled with the gas for 2–3 minutes at a gas supply rate of 5–10 liters per minute.

Then the tube is removed and through the opening 62 a mixture of monomers is poured into the sleeve 1. The volume of the mixture is preliminarily calculated on the basis of the required thickness of the gel shaped as a hollow cylinder. Immediately after filling, the drive 3 for rotation of the sleeve 1 is switched on and the rotation speed is increased to 800–900 r.p.m.

As a result, the solution of the monomers covers the entire inner surface of the side wall of the sleeve 1, but the gel thickness is not uniform along the height of the sleeve 1. Then the drive 65 is switched-on and the fixing member 66 is de-energized to turn the rotation axis of the sleeve 1 to the horizontal position. When the sleeve 1 reaches this position, the fixing member 67 is switched-on to fix the platform 4 in the horizontal position. In this position the mixture of the monomers coats the surface of the sleeve 1 in a uniform layer of the same thickness and even creeps into the slots formed by the longitudinal grooves of the annular insert 56 and the sleeve 1. The air bubbles are squeezed from these slots through the regions of the contacting surfaces of the annular insert 58, grooves 57 and the sleeve 1 by the solution of the monomers under the effect of centrifugal forces thereon. The rotation of the sleeve 1 in its horizontal position is effected for 20–30 minutes. During this time there occurs polymerization of monomers with the formation of a gel in the form of a hollow cylinder. Then the sleeve 1 is returned into the vertical position by means of the drive 65 and the lead 61 together with the sealing ring 60 are removed. This is the completion of the operation of the gel formation on the inner cylindrical surface of the sleeve 1 by way of pouring the solution of the monomers thereinto.

Then the sleeve 6 is placed into the sleeve 1 (FIG. 1) and rigidly connected therewith by joining the cantilever 7 with the platform 4, the sleeve 6 with the secured thereon annular electrodes 12 and 13, heat-exchanger 17 and receiver 22. Into the clearance between the side walls of the sleeves 1 and 6 first poured is the lower electrode solution 11 to a level positioned slightly below the sensor 23 of the receiver 22, whereafter the non-polar liquid 16 is poured to about half of the height of the annular insert 56, whereafter poured is the upper electrode solution 10 to the projection 63. The annular insert 58 is withdrawn by means of forceps and the recesses 15 are rinsed by means of a syringe using the electrode solution 10 to this end.

The water thermostat is then switched-on and the non-polar liquid 16 is heated to the required temperature usually equal to 323° K. (50° C.); the samples to be analyzed are introduced into the recesses 15 by means of a capillary in a volume of 1–2 $\mu$l and the required electric potential is applied to the annular electrodes 12 and 13 so that the electric field intensity be equal to 40–50 V/cm. Then the drive 3 of the sleeve 1 is switched on and the speed of its rotation is set equal to 20–30 r.p.m. Thereafter the source 20 of the monochromatic radiation, receiver 22 and recording unit 26 are switched-on. As a result, an electrophoretic separation of the samples starts under controllable temperature conditions and the source 20 with the receiver 22 are warmed-up to ensure their running-in to work under stable operation conditions and parameters.

Under the effect of the electric field the fragments of regions of the nucleic acid migrate in the direction of passage of electric current, i.e. from one end face to the other. Depending on the value of the charge and the size of the fragments, they acquire various velocities which results in separation of a mixture of fragments into individual groups of identical fragments, each of these groups being represented in the gel by an individual zone, while all the fragments of one sample form in the gel a track consisting of individual zones, said track passing from a recess 15 to the lower end face of the hollow cylinder. In the lower part of the gel 2 an optimal separation of these zones is attained and they can be recorded separately. For recording to molecules of nucleic acids during their electrophoretic separation, they are covalently added, in the course of preparation of samples, with molecules of a fluorescent substance serving as a tag.

When the leading zone reaches the region 24 of the gel, an automatic recording of the components of the analyzed samples starts which is effected by way of accumulation, in the memory unit 36 of the recording block 26, of the signals fed from the receiver 22 of the fluorescent radiation of the tags, for each of the tracks the signals are accumulated in a separate field of memory of the memory unit 36. The accumulated information can be presented on a video monitor and processed by means of a computer. A successive reading of the data fed into the memory unit 36 as a result of recording of the fluorescent radiation of the zones of four tracks wherein contained are the fragments of four termination reactions carried out for the same region of the polymeric chain of a nucleic acid makes it possible to establish the sequence of nucleotides or, in other words, the primary structure of the analyzed region of the nucleic acid.

The recording is effected in the following manner. At a switched-on drive 3 the signal supplied on the input 34 of the recording unit 26 from the base photodiode 33 through the pulse-former 42 is passed to the input 41 of the counter 39 and sets it into the zero state. The next signal passing from the sensor 5 of the turn angle of the sleeve is the address of the first track. This signal from the photodiode 35 via the pulse-former 44 is passed to the input 43 of the counter 39, is coded therein as "I" and a parallel code of the state of the counter 39 is transmitted via the bar into the address register 37. At the same time, the analog signal from the receiver 22 supplied to the information input 25 of the recording unit 26 and further to the input of the analog-to-digital convertor 40 is converted therein into a digital code which is passed into the data register 38 via a corresponding bar. The signal from the pulse-former 44 is also delivered onto the input of the generator 45, wherein with a delay relative to its input signal a reading signal is formed which is fed to the inputs 46 and 47 of the registers 37 and 38 and a signal for zero-setting of the registers 37 and 38 supplied onto the inputs 48 and 49 with a delay exceeding the delay of the reading signals relative to the input signal of the generator 45. In this case in one of the memory areas of the unit 36 the address of which is defined by the code read from the address register 37 the contents of the data register 38 is coded, whereafter the registers 37 and 38 are set into the zero state.

As the disk 28 rotates, into the photodiode 35 the following signal is fed which differs from the preceding signal by one unit and corresponds to the track No. 2. This signal is recorded in the counter 39, its state is put into the address register and the data recording process is repeated for the second track. In doing so, the data are memorized in another area of the memory unit 36. In a similar manner recording of signals from the receiver 22 of the monchromatic radiation is effected for all the remaining samples. The speed of rotation of the sleeve 1 is chosen so that the measurement of the fluorescent radiation for each zone be carried out for nearly ten times. This enables a minimized static error of the results of the electrophoretic determination of the sequence of nucleotides of the analyzed nucleic acids.

In order to increase productivity of determination of the primary structure by reducing the time of its carrying-out in the apparatus, it is possible to perform the procedure simultaneously in several plates of the gel having different concentration of acrylamide forming the hollow cylinder. The determination of the primary structure in the apparatus according to the present invention in this case is effected in the following manner.

After setting the annular inserts 56 and 58 and the sealing ring 60 into the sleeve 1 (FIG. 7) the lid 74 with the annular chamber secured thereto is also placed into the sleeve 1. The lid 74 is placed so that the radial partitions 72 (FIG. 8) be positioned opposite to the projections 68 of the sleeve 1, whereafter the lid 74 is fixed by means of fixing members in a manner similar to that described hereinabove. The sleeve 1 is filled with the inert gas as it has been already mentioned hereinbefore and then through the openings 76 (FIG. 7) in the lid 74 in the cavity 73 (FIG. 8) of the annular chamber 69 the solutions of the monomers are poured. The number of separately prepared solutions is equal to the number of cavities 73 and the solutions with the same concentration of acrylamide are poured into the cavities 73 positioned in the annular chamber 69 opposite to one another. In this manner, by means of the chamber 69 four plates of the gel are poured out of which two have a low, e.g. 8, concentration and two—a high, e.g. 16%, concentration of acrylamide.

Figure 7:
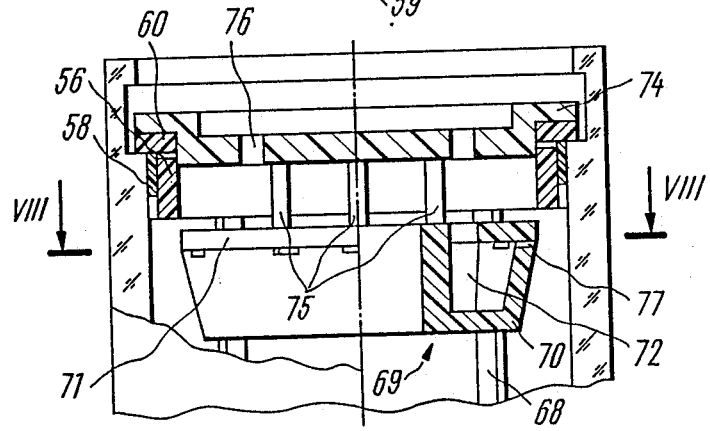
FIG. 7—a region of the main sleeve illustrating: an annular chamber, an annular insert with longitudinal grooves, an annular insert with projections and a lid (elevation view) according to the present invention.
Figure 8:
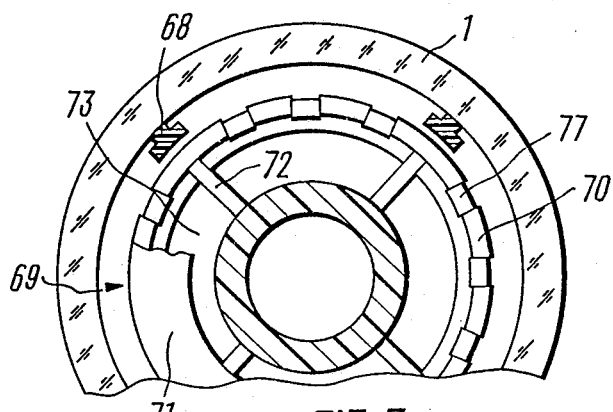
FIG. 8—a cross-section along the line VIII—VIII in FIG. 7.

The drive 3 (FIG. 3) is switched-on and with increasing the number of revolutions of the sleeve 1 the solutions of the monomers are poured out of the cavities 73 (FIG. 8) of the chamber 69 through the openings 77 owing to the effect of centrifugal forces onto the inner surface of the side wall of the sleeve 1 so that each solution is poured onto the region limited by the projections 68, the bottom of the sleeve 1 and the annular inserts 56 and 58 (FIG. 7). Rapidly growing centrifugal forces hinder the flowing of the solutions down onto the bottom of the sleeve 1. A further operation of the apparatus according to this embodiment of the present invention is similar to the above-described operation of the apparatus, except for the operation of introduction of the analyzed samples into the recesses 15 (FIG. 1). In the disclosed embodiment each sample is divided into two portions one of which is applied onto a gel plate with a low concentration of acrylamide and the other—onto a gel plate with a high concentration of acrylamide.

As it has been mentioned hereinabove, in the apparatus according to the present invention it is possible to use the gel 51 in the form of ready plates (FIG. 2). When the gel 51 is placed in the form of ready plates on the external surface of the side wall of the sleeve 1 the apparatus operates in the following manner.

The gel plates are fixed on the surface of the sleeve 1 by means of soft spring rings, whereafter the sleeve 1 with the drive 3 is placed into an additional sleeve 50 as it is shown in FIG. 2, i.e. coaxially with it and with a clearance relative this sleeve 50, the platform 4 with the drive 3 is rigidly secured on the sleeve 50. In further steps the operation of the apparatus and carrying-out of the process are similar to those described hereinbefore.

Furthermore, the use of ready plates of the gel is also possible in the apparatus according to the present invention in the embodiment thereof where the gel plates are positioned on the inner surface of the side wall of the sleeve 1. In this embodiment of the apparatus its operation is as follows.

The ready gel plates are cut so that their height be somewhat longer than the length of the projections 68 (FIG. 3) and the width be equal to the length of the arc between two adjacent projections 68 (FIG. 6) on the inner surface of the side wall of the sleeve 1. Then, by bending the plate, it is fitted by its side edges into the grooves formed by the T-like (in cross-section) projections 68 and the inner surface of the side wall of the sleeve 1, whereafter the gel plate is pressed to the surface of the sleeve 1. In this case it is not necessary to use the annular insert 56 (FIG. 3) and it is not mounted in the sleeve 1. Then the operation of the apparatus and the determination of the primary structure of nucleic acids is effected in a manner similar to that for the embodiment described hereinbefore.

For a better understanding of the present invention some specific examples illustrating the process for an electrophoretic determination of the primary structure of nucleic acids are given hereinabelow with reference to the above-described embodiments of operation of the apparatus realizing this process.

EXAMPLE 1

The preparation of the apparatus for pouring into the sleeve 1 (FIG. 1) of a solution of monomers was effected according to the procedure of the above-described embodiment. The solution of the monomers was prepared in the volume of 36 ml to obtain the gel 2 in the form of a hollow cylinder with the thickness of 0.3 mm in the sleeve 1 having the inside diameter of 200 mm and the height of the surface for placing the gel 2—200 mm. The solution of the monomers for carrying out the sequencing electrophoresis in a 8% polyacrylamide gel under denaturation conditions contained in 36 ml of the solution 2.9 g of acrylamide, 0.15 g of methylenebisacrylamide, 0.036 ml of tetramethylethylenediamine, 0.018 g of ammonium persulphate, 0.39 g of trishydroxyethylaminomethane, 0.2 g of boric acid, 0.035 g of sodium ethylenediaminetetracetate and 15.1 g of urea.

Then the solution of the monomers immediately after its preparation (ammonium persulphate and tetramethylethylenediamine are added last) is poured into the sleeve 1 and operations of polymerization of the gel 2 are performed following the procedure described hereinabove. The gel 2 after polymerization of the solution of the monomers has a shape of a hollow cylinder and a smooth surface without the residues of the liquid phase.

The employed electrode solutions had the following composition. The electrode solution 10 (the upper solution): 1 litre of the solution 10 contained: 10.8 g of trishydroxyethylaminomethane, 5.5 g of boric acid, 0.93 g of sodium ethylenediaminotetracetate and its pH was 8.3. The electrode solution 11 (the lower solution) had the same components and additionally contained in 1 liter 260 g of saccharose. As the non-polar liquid 16 use was made of a mixture of hexane and carbon tetrachloride of the density of $1.06 \pm 0.02$ g/cm$^3$.

The solutions are poured in the sequence mentioned in the description of operation of the apparatus shown in FIG. 1, whereafter the remaining operations are carried out till the application of samples onto the gel 2.

Into each recess 15 1.5 µl of the electrode solution 10 is introduced which contains: urea (7M) and 0.025% of each of the following tag dyes: bromophenol blue and xylenecyanol, whereafter onto the annular electrodes 12 and 13 an electric potential is fed. The electrophoresis is carried out at the voltage of 650 V, the current through the gel 2 is 70–75 mA. The speed of the dye movement is as follows: for bromophenol blue having an electrophoretic mobility equivalent to that of DNA or RNA molecules of 25–30 nucleotides length—175 mm/h, for xylenecyanol having a mobility equivalent to that of molecules of 70–85 nucleotides length—93 mm/h. The results of measurement of the distance passed by the dyes within 1 and 2 hours in all of the gel tracks have given the range of values of 0.3–0.5 mm for 160 tracks which upon resolution of the zones equal to 1.2–1.4 attained in the gel shaped as a hollow cylinder of the above-specified length corresponds to an error of the electrophoretic analysis of less than 0.2% for 4 adjacent tracks.

EXAMPLE 2

The preparation of fluorophor-tagged samples for the determination of the primary DNA structure by the method of an electrophoretic determination of the primary structure of nucleic acids in the apparatus according to the present invention is effected in the following manner.

A set of fragments of a sequenced DNA molecule is obtained by the method of termination of the reaction of polymerase copying of DNA after Sanger. For the purpose of tagging the DNA with the fluorophor use is made of a chemically synthesized oligonucleotide primer conjugated with tetramethylrhodamine.

The synthesis of the DNA fragments is effected in the system of the phage M13. To 2 µl of a solution containing about 0.2 pM of the analyzed DNA 0.6 pM of the tagged primer is added in the volume of 0.5 µl. The primer is dissolved in a 10-fold buffer solution of the following composition: 0.5M of NaCl, 66 mM of trishydroxyethylaminomethane with the pH of 7.4, 66 mM of MgCl$_2$, 10 mM of dithiothreitol. The resulting mixture is thoroughly stirred and placed on a refluxing water bath of 500 ml volume for 3 minutes. Then the water bath is switched-off and allowed to cool to room temperature which takes approximately 2 hours. On completion of the reaction in the reaction mixture there are formed hybrid molecules of the DNA+primer. Then the mixture is added, to the final volume of 10 µl, with a buffer solution of the following composition: 50 mM of trishydroxyethylaminomethane with the pH of 8.5, 5 mM of MgCl$_2$, 2 mM of dithiothreitol. The thus-diluted mixture is divided into portions of 2 µl charged each into 4 test-tubes for carrying out the reaction of termination of polymerase copying for 4 bases.

Into each test-tube there is added 1 µl of a mixture of deoxyribonucleosidetriphosphates (dATP, dCTP, dGTP, dTTP) with the concentration of each of 0.125 mM and 1 µl of corresponding dideoxyribonucleosidetriphosphates (ddATP, ddCTP, ddGTP, ddTTP) in the following molar proportions:

dATP/ddATP=1,
dCTP/ddCTP=2.5
dGTP/ddGTP=6,
dTTP/ddTTP=6.

Into each test-tube there is added 1 µl of a solution of polymerase (Klenov's fragment) with the specific activity of 1 unit/µl, thoroughly intermixed and incubated at the temperature of 37° C. for 15 minutes. Then into each sample 1 µl of the mixture of dATP, dCTP, dGTP and dTTP is added in the concentration of each of 0.5 mM and incubation is continued for additional 15 minutes. The reaction is terminated by the addition of 5 µl of a 99% solution of formamide with the dyes: bromophenol blue and xylenecyanol (0.5% of each) and 20 mM of ethylenediaminotetracetate. The molecules of the analyzed DNA and of the fragments are subjected to denaturation under these conditions.

The gel 2 is polymerized in the sleeve 1 and the electrode solutions 10 and 11, as well as the non-polar liquid 16 are poured thereinto as described hereinabove. The previously prepared samples are refluxed for 3 minutes and then applied onto the gel 2. Into each recess 15 2 µl of the analyzed sample are introduced and the electrophoretic separation and recording of the fragments of the samples is carried out as described hereinbefore for the embodiment of the apparatus according to the present invention. Upon the recording in the apparatus use is made of an argon laser as the source 20 of a monochromatic radiation. For isolation of the fluorescent radiation use is made of an interference filter with the maximum of the transmittance spectrum at 520 nm.

In the present invention the use of the principle of a radial symmetry upon placing a gel shaped as a hollow cylinder upon its thermostatting and recording of fragments of samples makes it possible to improve the productivity and quality of the process and simplify the apparatus for its implementation. For example, at a diameter of a sleeve on the side surface of which a gel is located equal to 240 mm the determination of the primary structure can be effected on 160 tracks, i.e. to simultaneously analyze the primary structure of 40 fragments of DNA of 300 nucleotides length each. This corresponds to the productivity of sequencing equal to 25,000–30,000 nucleotides a day, i.e. by 25–30 times higher than in the prior art apparatus. An increase of the hollow cylinder diameter, in order to ensure a further improvement of the process productivity, will result in an increase of the sleeve diameter only by $\frac{1}{3}$.

The error in the determination of the primary structure in the case of using the present invention is by 10–12 times lower than in the case of using the prior art process and apparatus. However, this is not the only indicator for an improved quality. It is also necessary to take into consideration the factors which are not apt to a direct quantification. They may be exemplified by a reduced probability of critical situations and breakdowns, as well as a diminished influence of destabilizing factors on the process of determination of the primary structure. This can be also exemplified by reduced requirements to the skill of the operating personnel. All this will make it possible to additionally lower the measurement errors due to an increased reliability of the process and of the apparatus and due to their simplification.

What is claimed is:

1. A process for electrophoretic determination of the primary structure of a nucleic acid comprising:
   (a) preparing samples of a nucleic acid in the form of fragments of its polymeric claim containing tags;
   (b) placing the samples into recesses located on a circumference of an end face of a gel in a shape of a hollow cylinder;
   (c) applying an electrical potential to the end faces of the hollow cylinder for an electrophoretic separation of said fragments in the direction of passage of an electric current in accordance with the size of said fragments;
   (d) maintaining said gel at a constant temperature level at which movement of said fragments is effected without their chemical combination at hydrogen bonds, by providing a layer of a temperature controlled non-polar liquid, located on one side of a lateral surface of the hallow cylinder, and wherein the non-polar liquid layer is of a height about equal to the height of the hollow cylinder;
   (e) recording said fragments according to their tags by rotating said gel shaped as a hollow cylinder around its axis to determine a relative position of said fragments in said gel to determine the sequence of nucleotides in the nucleic acid molecule.

2. A process of claim 1 which includes placing a layer of a polymeric material resistant to the non-polar liquid between said gel shaped as a hollow-cylinder and said layer of the non-polar liquid.

3. A process of claim 1, comprising:
   (a) shaping said gel as a hollow cylinder having a different porosity in individual regions located around its circumference;
   (b) preparing at least two identical samples containing identical fragments of identical regions of its polymeric chain; and
   (b) placing said identical samples onto said regions of said gel having different porosity.

4. A process of claim 3, which comprises placing a layer of a polymeric material resistant to the non-polar liquid between said gel, shaped as a hollow cylinder and said layer of the non-polar liquid.

5. An apparatus for the electrophoretic determination of the primary structure of nucleic acids comprising:
   (a) a cylindrically-shaped cuvette formed from a dielectric material vertically mounted as a first sleeve; a gel shaped as a hollow cylinder placed adjacent a bottom and a side wall of the first sleeve;
   (b) a drive for rotation of said first sleeve around an axis thereof connected with the first sleeve;
   (c) a platform on which said drive is mounted;
   (d) a first chamber and a second chamber positioned in the upper and lower parts of the first sleeve and communicating with the first sleeve;
   (e) a second sleeve formed from a dielectric material having a side wall and a bottom fixedly mounted coaxially with the first sleeve on said platform, said side walls and said bottoms of the first and the second sleeves forming the first and the second chambers;
   (f) a first and a second electrode solution, the first electrode solution being located between said bottom and said side walls of the first and second sleeves in the region adjacent to said bottom of said sleeves, in contact with the gel and the second electrode solution located in the upper part of the first and second sleeves between their side walls in contact with the gel;
   (g) a first and a second annular electrode positioned coaxially with the first and second sleeves; the first annular electrode being in contact with the first electrode solution and the second annular electrode being in contact with the second electrode solution;
   (h) a source of electric potential to which the first and second annular electrodes are connected;
   (i) a means for controlling the temperature of the gel comprising a non-polar liquid positioned between the first and the second electrode solutions in the region between said side walls of the first and second sleeves and a heat-exchanger means located in said non-polar liquid, the first electrode solution having a higher density than the density of said non-polar liquid and the second electrode solution being located above said non-polar liquid having a lower density than the non-polar liquid;
   (j) a source of a monochromatic radiation with its light beam directed into the gel for exciting a fluorescent radiation;
   (k) a detector of the fluorescent radiation having a sensor facing the region of said gel illuminated by said source; the detector having an output;
   (l) a recording unit having an information input and an address input, to the information input of which unit said output of said detector is connected
   (m) a sensor of the turn angle of the first sleeve having an output connected to said address input of said recording unit.

6. An apparatus of claim 5, wherein said source of the monochromatic radiation is mounted so that its light beam is directed to said bottom of the first or the second sleeve, said bottom being made from a material optically transparent for the monochromatic radiation.

7. An apparatus for electrophoretic determination of the primary structure of nucleic acids comprising:
  (a) a cylindrically-shaped cuvette formed from a dielectric material vertically mounted as a first sleeve; a gel shaped as a hollow cylinder placed adjacent a bottom and a side wall of the first sleeve;
  (b) a drive for rotation of said first sleeve around an axis thereof connected with the first sleeve;
  (c) a platform on which said drive is mounted;
  (d) a first chamber and a second chamber positioned in the upper and lower parts of the first sleeve and communicating with the first sleeve;
  (e) a second sleeve formed from a dielectric material having a side wall and a bottom fixedly mounted coaxially with the first sleeve on said platform, said side walls and said bottoms of the first and the second sleeves forming the first and the second chambers;
  (f) a first and a second electrode solution, the first electrode solution being located between said bottom and said side walls of the first and second sleeves in the region adjacent to said bottom of said sleeves, in contact with the gel and the second electrode solution located in the upper part of the first and second sleeves between their side walls in contact with the gel;
  (g) a first and a second annular electrode positioned coaxially with the first and second sleeves; the first annular electrode being in contact with the first electrode solution and the second annular electrode being in contact with the second electrode solution;
  (h) a source of electric potential to which the first and second annular electrodes are connected;
  (i) a means for controlling the temperature of the gel comprising a non-polar liquid positioned between the first and the second electrode solutions in the region between said side walls of the first and second sleeves and a heat-exchanger means located in said non-polar liquid, the first electrode solution having a higher density than the density of said non-polar liquid and the second electrode solution located above said non-polar liquid having a lower density than the non-polar liquid
  (j) a source of a monochromatic radiation with its light beam directed into the gel for exciting a fluorescent radiation;
  (k) a detector of the fluorescent radiation having a sensor facing the region of said gel illuminated by said source; the detector having an output;
  (l) a recording unit having an information input and an address input, to the information input of which unit said output of said detector is connected
  (m) a sensor of the turn angle of the first sleeve having an output connected to said address input of said recording unit
  (n) a means for shaping said gel from a solution of monomers as a hollow cylinder which is represented by the first sleeve with said drive for its rotation around the axis;
  (o) a means for making recesses on the end face of the hollow cylinder mounted in the first sleeve upon shaping of the gel until the completion of the gel shaping; a first annular insert of said means for making recesses provided in the upper part of the first sleeve; longitudinal grooves made on the external cylindrical surface of the first annular insert forming slots between said annular insert and the inner surface of said side wall of the first sleeve;
  (p) a second annular insert of said means for making recesses on the end face of which insert projections are made along its perimeter and positioned in said slots; a sealing ring of said means for making recesses positioned above the second annular insert; a lid of said means for making recesses provided on the end face of the first sleeve, wherein an opening is made to pour a solution of monomers into the first sleeve.

8. An apparatus for an electrophoretic determination of the primary structure as claimed in claim 7, comprising:
  (a) said platform rotatably mounted to turn to 90° in the vertical plane;
  (b) a first and a second fixing members for extreme positions of said platform.

9. An apparatus of claim 8, wherein the inner surface of said side wall of the first sleeve is shaped as a tapered cone facing said bottom of said first sleeve with its greater base.

10. An apparatus of claim 8, wherein on the inner surface of said side wall of the first sleeve along the generatrix from said bottom of the first sleeve to the region of mounting of the first annular insert projections are made which are uniformly positioned in a circle.

11. An apparatus of claim 10, wherein said projections on the inner surface of said side wall of the first sleeve have a T-like shape in their cross-section.

12. An apparatus of claim 11 comprising:
  (a) an annular chamber having a trapezoidal shape in its cross-section mounted under the first annular insert, rigidly connected with said lid and facing it with the greater base of the trapezium; an external side wall of said chamber;
  (b) a group of radial partitions of said annular chamber according to the number of said projections made on the inner surface of said side wall of the first sleeve positioned uniformly along the circumference and forming cavities for containing solutions of monomers with different concentration;
  (c) a group of openings according to the number of said cavities made in the upper part of said external side wall of said annular chamber intended for outflow of solutions of monomers onto respective regions of the inner surface of said side wall of the first sleeve limited by said projections.

13. An apparatus of claim 7, wherein the inner surface of said side wall of the first sleeve is shaped as a tapered cone facing said bottom of said first sleeve with its greater base.

14. An apparatus of claim 7, wherein on the inner surface of said side wall of the first sleeve along the generatrix from said bottom of the first sleeve to the region of mounting of the first annular insert projections are made which are uniformly positioned in a circle.

15. An apparatus of claim 14, wherein said projections on the inner surface of said side wall of the first sleeve have a T-like form in the cross-section thereof.

16. An apparatus of claim 15, comprising:
  (a) an annular chamber having a trapezoidal shape in its cross-section mounted before the first annular insert rigidly connected with said lid and facing it with the greater base of the trapezium; an external side wall of said chamber;

(b) radial partitions of said annular chamber according to the number of said projections made on the inner surface of said side wall of the first sleeve uniformly positioned along the circumference and forming cavities for containing solutions of monomers with different concentrations;

(c) a group of openings according to the number of said cavities made in the upper part of said side wall of said annular chamber intended for outflow of the solutions of the monomers onto respective regions of the inner surface of said side wall of the first sleeve limited by said projections.

* * * * *